United States Patent [19]

Miyayama et al.

[11] Patent Number: 5,576,067
[45] Date of Patent: Nov. 19, 1996

[54] CARBON MONOXIDE (CO) DETECTING SENSOR, AND MANUFACTURING PROCESS THEREFOR

[75] Inventors: Masaru Miyayama, Kawasaki, Japan; Byoung C. Shin, Pohang, Rep. of Korea

[73] Assignees: Pohang Iron & Steel Co., Ltd.; Research Institute of Industrial Science & Technology, both of Kyong Sang Book-Do, Rep. of Korea

[21] Appl. No.: 392,845

[22] PCT Filed: Jul. 1, 1994

[86] PCT No.: PCT/KR94/00083

§ 371 Date: Mar. 1, 1995

§ 102(e) Date: Mar. 1, 1995

[87] PCT Pub. No.: WO95/01565

PCT Pub. Date: Jan. 12, 1995

[30] Foreign Application Priority Data

Jul. 2, 1993 [KR] Rep. of Korea ............... 1993/12395

[51] Int. Cl.[6] .................. G01N 27/12; G01N 27/26
[52] U.S. Cl. .................. 427/443.2; 204/424; 264/56; 427/123; 427/125; 427/126.3; 427/226; 427/372.2; 427/383.1; 427/383.3; 427/404; 427/419.2
[58] Field of Search ................... 204/421–429; 427/443.2, 123, 125, 126.1, 126.3, 226, 372.2, 383.1, 383.3, 404, 419.2, 422/98; 264/56

[56] References Cited

U.S. PATENT DOCUMENTS

| | | | |
|---|---|---|---|
| 3,821,981 | 7/1974 | O'Neill et al. | 427/443.2 |
| 3,944,683 | 3/1976 | Church et al. | 427/443.2 |
| 4,372,824 | 2/1983 | Toda et al. | 204/427 |
| 4,940,528 | 7/1990 | Oki et al. | 204/428 |
| 5,120,575 | 6/1992 | Ferrando et al. | 427/443.2 |

FOREIGN PATENT DOCUMENTS 62-90529  1/1986  Japan.

OTHER PUBLICATIONS

Y. Nakamura, H. Yoshioka, M. Miyayama, H. Yanagida, T. Tsurutani and Y. Nakamura, "Selective CO Gas Sensing Mechanism with CuO/ZnO Heterocontact", *J. Electrochem. Soc.*, vol. 137, No. 3, Mar. 1990, pp. 940–943.

Y. Nakamura, T. Tsurutani, M. Miyayama, O. Okada, K. Koumoto and H. Yanagida, "The Detection of Carbon Monoxide by the Oxide–Semiconductor Hetero–Contacts", *The Chemical Society of Japan*, 1987, month unavailable No. 3, pp. 477–483.

*Primary Examiner*—T. Tung
*Attorney, Agent, or Firm*—Webb Ziesenheim Bruening Logsdon Orkin & Hanson P.C.

[57] ABSTRACT

A CO gas detecting sensor for detecting the existence or absence of CO gas and a manufacturing process therefor are disclosed. The CO gas detecting sensor includes: a sintered zinc oxide body; a copper oxide coating layer formed on a side of the sintered zinc oxide body; a positive metal electrode layer (a first electrode layer) electrically connected to the copper oxide coating layer; and a negative metal electrode layer (a second electrode layer) formed on the other side of the sintered zinc oxide body. The CO gas detecting sensor according to the present invention is superior in the preference for CO gas, and has an improved measuring repeatability, as well as a superior sensitivity.

1 Claim, 3 Drawing Sheets

CARBON MONOXIDE (CO) DETECTING SENSOR, AND MANUFACTURING PROCESS THEREFOR

FIELD OF THE INVENTION

The present invention relates to a carbon monoxide (CO) detecting sensor for detecting the existence and absence of carbon monoxide, and a manufacturing process therefor.

BACKGROUND OF THE INVENTION

Generally, a steel manufacturing plant generates gases which are harmful to the human body, and among these gases, CO gas is a dangerous one which can give a fatal inflict to the human body even at a concentration of less than 2000 ppm.

Conventionally there have been developed various CO gas detecting sensors for detecting the existence and absence of CO gas, but the $SnO_2$ series CO gas detecting sensor which is currently used operates in the following manner. That is, an oxygen ion ($O^-$) which has been adhered on the surface of the gas is desorbed by being reacted with a reactive gas, and therefore, the electron which has been captured by the oxygen ion is converted to a free electron, with the result that the conductivity of the gas is increased. This conductivity is measured, and the existence of CO gas is determined. However, this CO gas detecting sensor has a disadvantage that it is reacted with even hydrogen gas or propane gas (Japanese Chemical Journal 1987, No. 3, p447–488).

Meanwhile, recently, there has been developed another CO gas detecting sensor in which a p type semiconductor (CuO) and an n type semiconductor (ZnO) are physically contacted. According to Japanese Patent Laid-open No. Sho-62-90529, the CO gas detecting sensor has the advantage that it has the selectivity of reacting only with CO gas. However, it consists of two different semiconductors contacted together, and the two semiconductors are separated after the measurement. Therefore, when CO gas is to be measured again, a perfect contact realization of the two semiconductors are very low, with the result that the sensitivity for the measurement of CO gas is apt to be varied.

SUMMARY OF THE INVENTION

The present invention is intended to overcome the above described disadvantages of the conventional techniques.

Therefore it is the object of the present invention to provide a CO gas detecting sensor and a manufacturing process therefor, in which the CO gas preference is greatly improved compared with the conventional $SnO_2$ series CO gas detecting sensor, and the measurement repeatability is greatly improved compared with the conventional p-n combination type CO gas detecting sensor.

In achieving the above object, the CO gas detecting sensor according to the present invention includes: a sintered zinc oxide (ZnO) body; a copper oxide (CuO) coating layer formed on a side of the sintered zinc oxide body; a positive metal electrode layer electrically connected to the copper oxide coating layer; and a negative metal electrode layer formed on the other side of the sintered zinc oxide body.

In achieving the above object, the process for manufacturing the CO gas detecting sensor according to the present invention comprises the steps of: press-forming a zinc oxide powder in the usual manner, and sintering it at 650–1000° C. for 30 minutes to 3 hours; dipping a portion of the sintered zinc oxide body into an aqueous copper nitrate ($Cu(NO_3)_3H_2O$) solution to form a composite semiconductor; heat-treating the composite semiconductor for converting the copper nitrate of the composite semiconductor into copper oxide so as to form a thin copper oxide layer; spreading a metal on the copper oxide layer and on the portion of the sintered zinc oxide body where no copper oxide layer is formed, so as to form positive and negative electrodes; and heat-treating the positive and negative electrodes.

BRIEF DESCRIPTION OF THE DRAWINGS

The above object and other advantages of the present invention will become more apparent by describing in detail the preferred embodiment of the present invention with reference to the attached drawings in which.

DESCRIPTION OF THE PREFERRED EMBODIMENT

Figure 1:
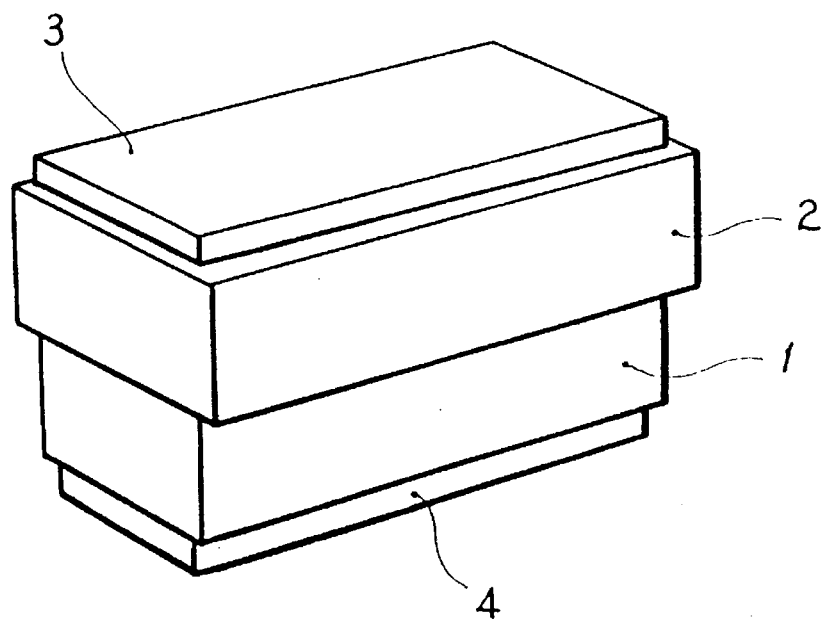
FIG. 1A and 1B are respectively a perspective view and a sectional view showing the schematic constitution of the CO gas detecting sensor according to the present invention.
Figure 1:
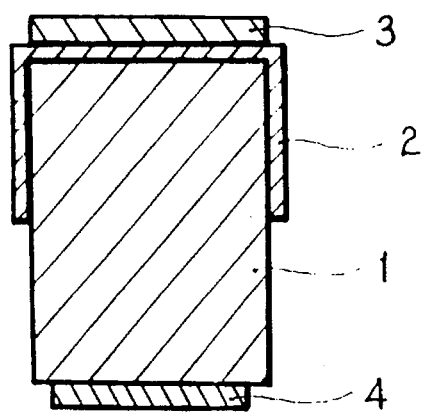

FIG. 1 schematically illustrates the constitution of the preferred embodiment of the CO gas detecting sensor according to the present invention, and FIG. 1A is a perspective view, while FIG. 1B is a sectional view.

The CO gas detecting sensor according to the present invention is constituted such that a copper oxide coating layer 2 is formed on the top of a zinc oxide sintered body 1, and a positive electrode layer 3 composed of silver and a negative electrode layer 4 composed of a mixture of silver and zinc are formed respectively on the top of the copper oxide coating layer and on the bottom of the sintered zinc oxide body.

The positive electrode layer of the CO gas detecting sensor should be preferably composed of silver (Ag) in view of the electric conductivity and the coating adhering characteristics. However, besides silver, other electrically well conducting materials can be used. The negative electrode layer should be preferably composed of a mixture of silver and zinc, and the reason is that this material has a low contact resistance, and that electrons can be easily released. If the electrode layer is composed of only silver and not the mixture of silver and zinc, the current-voltage curve becomes non-linear. This means that the contact resistance is large, and therefore, it is not desirable.

In manufacturing the CO gas detecting sensor according to the present invention, it is desirable first to press-form a zinc oxide powder, and to carry out a sintering at a temperature of 650–1000° C. for 30 minutes to 3 hours. If the press-formed body is sintered at a temperature below 650°

C. and for less than 30 minutes, the sintering is not realized at all owing to the inherent characteristics of zinc oxide. If the sintering is carried out at a temperature of over 1000° C. and for more than 3 hours, the relative density becomes over 95%, so that, at a later step, the impregnation of copper nitrate ($Cu(NO_3)^3H_2O$) should become impossible.

A portion of the zinc oxide sintered body is dipped into an aqueous copper nitrate solution so as to form a composite semiconductor, and this composite semiconductor is heat-treated to convert the surface layer of the copper nitrate into copper oxide. The heat treatment should be preferably carried out at a temperature of 470–800° C. for 10 minutes to 2 hours. If the heat treatment is carried out at a temperature of below 470° C. for less than 10 minutes, the copper nitrate can barely converted into copper oxide, because the decomposing temperature of copper nitrate is about 450° C. On the other hand, if the heat treatment is carried out at a temperature of over 800° C. for more than 2 hours, then the particles of copper oxide are excessively grown so as to reduce the contact areas of the zinc oxide, copper oxide and the externally introduced gas, with the result that the measuring sensitivity is lowered, and that the CO gas preference is deficient, thereby making it undesirable.

Then an electrode layer composed of silver and zinc is formed on a side of the sintered zinc oxide body, and an electrically conductive electrode layer is coated on a side of the copper oxide. Then a heat treatment is carried out, and the heat treatment should be preferably carried out at a temperature of 550–700° C. for 10 minutes to 1 hour. If the heat treatment is carried out at a temperature below 550° C. for less than 10 minutes, the coated electrode layer is peeled off. On the other hand, if the heat treatment is carried out at a temperature of over 700° C. for more than 1 hour, then the coated electrode layer intrudes into the sintered body, with the result that the silver electrode layer and the sintered zinc oxide body are directly merged, and that the effect of capturing CO gas by the copper oxide layer is reduced, thereby making it undesirable.

Now the present invention will be described based on an actual example referring to the attached drawings.

First, a zinc oxide powder having an average particle diameter of 1 μm was press-formed with a pressure of 1 kgf/mm², thereby making a plurality of zinc oxide bodies. Then sinterings were carried out at a temperature of 600–1200° C. for 30 minutes, for 1 hour, and for 3 hours respectively. Then the sintering characteristics of the sintered zinc oxide bodies were inspected with human eyes, and the pore rate was also measured, the results being shown in Table 1 below.

TABLE 1

| Sintg Time | Sintg Temp | | | | |
|---|---|---|---|---|---|
|  | 600° C. | 650° C. | 800° C. | 1000° C. | 1200° C. |
| 30 minutes | x | 70% | 80% | 84% | 95% |
| 1 hour | x | 75% | 82% | 84% | 95% |
| 3 hours | x | 75% | 82% | 85% | 95% | x represents the case in which the sintering was impossible.
%: the measured density rate relative to the theoretical density.

Then, the sintered zinc oxide body 1 was dipped into an aqueous copper nitrate solution so as to form a thin composite semiconductor layer on a side of the sintered body through deposition of the copper nitrate thereon. Then heat treatments were carried out at a temperature of 450–1000° C. respectively for 10 minutes, for 1 hour, and for 2 hours, thereby converting the thin layer of copper nitrate into a thin copper oxide layer. Then the current amount versus the gas flow was measured, and the results are shown in Table 2 below.

TABLE 2

| Time | Heat treatmt Temp. | | | | | | | | | | | |
|---|---|---|---|---|---|---|---|---|---|---|---|---|
|  | 450° C. | | 500° C. | | 550° C. | | 600° C. | | 800° C. | | 1000° C. | |
|  | Sensitivity | Selectivity | Sensitivity | Selectivity | Sensitivity | Selectivity | Sensitivity | Selectivity | Sensitivity | Selectivity | Sensitivity | Selectivity |
| 10 min. | X | X | O | O | O | O | O | O | O | Δ | O | X |
| 1 hour | X | X | O | O | O | O | O | O | O | Δ | O | X |
| 2 hours | X | X | O | O | O | O | O | O | O | Δ | O | X |

X: No Good.
Δ: Good.
O: Extremely good.

Then silver was spread on the upper side of the thin copper oxide layer, while silver mixed with zinc was spread on the bottom of the sintered zinc oxide body 1. Then heat treatments were carried out at temperatures of 500° C., 550° C., 600° C., 70° C. and 800° C. for 10 minutes, for 30 minutes and for 1 hour respectively, thereby forming a silver electrode 3 and silver-zinc electrode 4. Then the close contact of the electrodes were measured with human eyes, and the impregnation was measured with a scanning electron microscope, the results being shown in Table 3 below.

TABLE 3

| Heat treat temp | 500° C. | 550° C. | 600° C. | 700° C. | 800° C. |
|---|---|---|---|---|---|
| 10 minutes | Peeled | Good | Good | Good | Impregnated |
| 30 minutes | " | " | " | " | " |
| 1 hour | " | " | " | " | " |

As can be seen in Table 1 above, if the sintering temperature was below 600° C., the measured density rate relative to the theoretical density was less than 70%, with the result that the sintering becomes impossible. Further, the sintering and the impregnation state was good within the range of 650–1000° C. If the sintering temperature is higher than 1200° C., the measured density rate relative to the theoretical density was too high, with the result that the impregnations becomes impossible.

Further, as shown in Table 2, the gas sensitivity and the gas preference versus the heat treatment temperature and the time were bad at a temperature of 450° C. Meanwhile, at a temperature of 1000° C., the gas sensitivity was good, but the preference was bad.

Further, as shown in Table 3 above, the electrode layer was peeled off, and therefore, the close contact was not perfect. At a temperature of 800° C., impregnation occurred, and therefore, the silver electrode and the sintered zinc oxide body were electrically connected, with the result that the CO gas capturing effect of the copper oxide layer was dissipated.

The evaluation results for the CO gas detecting sensor which was manufactured under the proper conditions are as follows.

Figure 2:
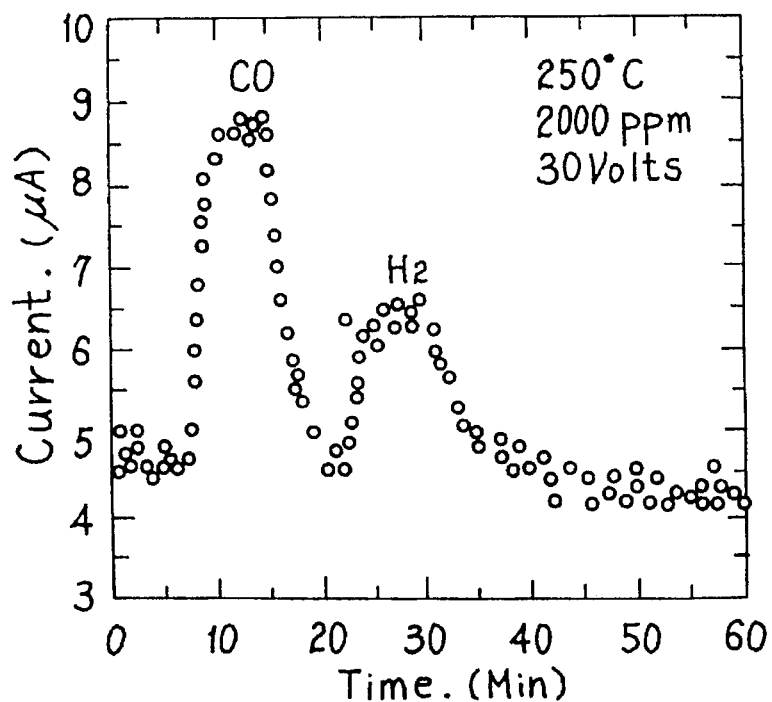
FIGS. 2A and 2B are graphical illustrations showing the current variations measured by the CO gas detecting sensor respectively under CO gas atmosphere and a hydrogen gas atmosphere at 250° C. and 400° C.
Figure 2:
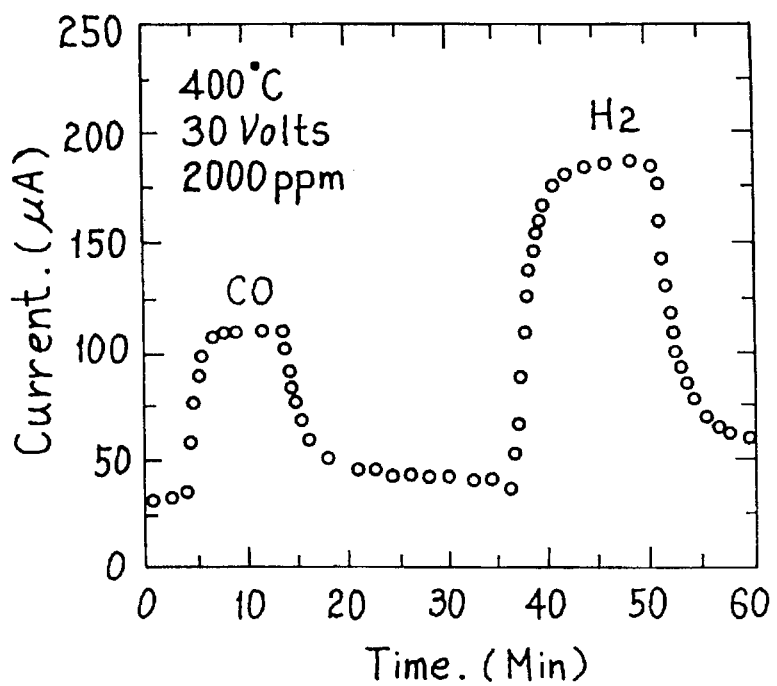

An amount of air containing 2000 ppm of CO and an amount of air containing 2000 ppm of $H_2$ were injected at different time points keeping the temperature at 250° C. Then a dc voltage of 30 V was supplied to the opposite sides of the electrodes of the CO gas sensor, and then, the variation of the current was measured, and the results are shown in FIG. 2A. As shown in FIG. 2A, the current flow for the CO gas was 9 μA, and the current flow for $H_2$ was 6.5 μA. Thus it is confirmed that the sensitivity for CO is greater than that for $H_2$. Further, the current flow was measured at a temperature of 400° C. in the same manner, and the results are shown in FIG. 2B. As shown in FIG. 2B, the current flow for CO was about 130 μA, and the current flow for $H_2$ was about 190 μA. Thus it is confirmed that the sensitivity for CO is lower than that for $H_2$.

Figure 3:
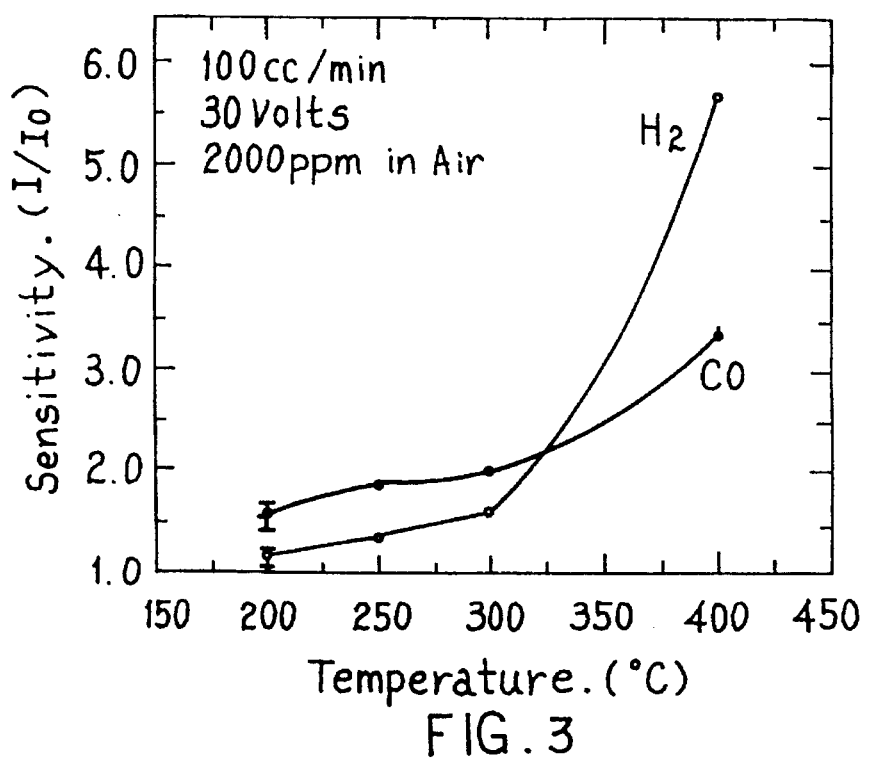
FIG. 3 is a graphical illustration showing the sensitivity variation versus the measuring temperature, the measurement being carried out under a CO gas atmosphere and under a hydrogen atmosphere by the CO gas detecting sensor according to the present invention.

FIG. 3 illustrates the results of measuring the variation of the sensitivity under the same manner, but varying the measuring temperature within a range of 200–400° C. According to FIG. 3, the preference for CO existed below 300° C., while the preference for CO did not exist above 350° C., because the sensitivity for $H_2$ was greater than that for CO. Further, it was impractical at 200° C., because the reaction speed was not only slow, but the deviations were large.

Figure 4:
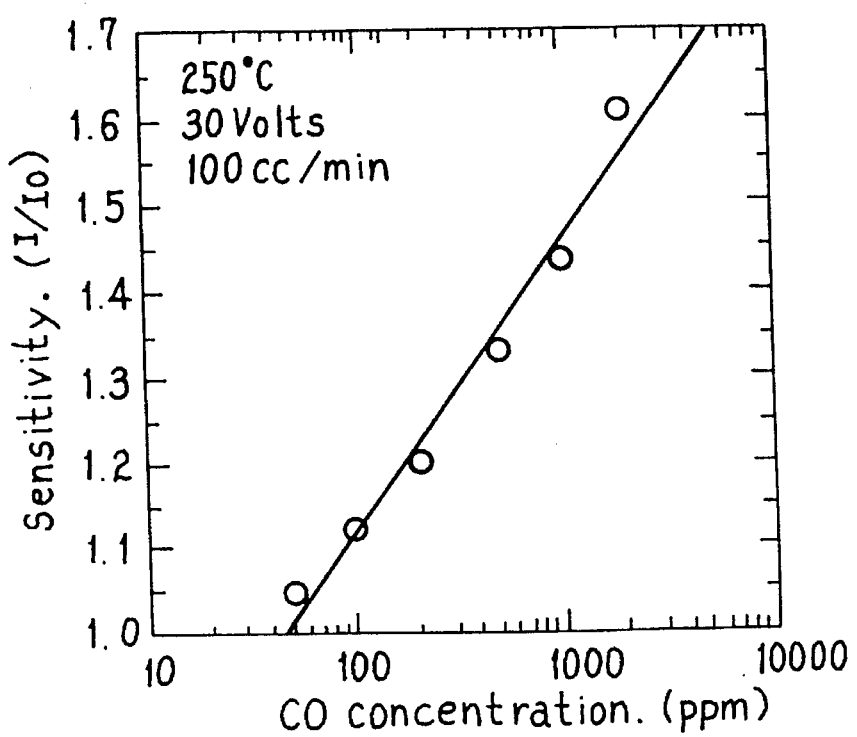
FIG. 4 is a graphical illustration showing the sensitivity variation versus the CO gas concentration for the CO gas detecting sensor according to the present invention.

Meanwhile, as shown in FIG. 4, the sensitivity versus the concentration of the CO gas contained in the air could be measured even at a temperature of 250° C. and down to 50 ppm.

According to the present invention as described above, the CO gas detecting sensor is superior in the preference for CO gas compared with the conventional $SnO_2$ series CO gas detecting sensor. Further, its repeatability for the measuring characteristics is improved compared with the conventional CuO/ZnO series CO gas detecting sensor. Thus the CO gas detecting sensor according to the present invention is capable of measuring CO gas down to a concentration of 50 ppm which is the legally regulated level.

What is claimed is:

1. A process for manufacturing a CO gas detecting sensor, comprising the steps of:

press-forming a zinc oxide powder and sintering at 650°–1000° C. for 30 minutes to 3 hours to form a sintered zinc oxide body;

dipping a portion of the sintered zinc oxide body into an aqueous copper nitrate solution to form a composite semiconductor;

heat-treating the composite semiconductor at a temperature of 470°–800° C. for 10 minutes to 2 hours for converting the copper nitrate of the composite semiconductor into copper oxide so as to form a thin copper oxide layer;

spreading silver on the copper oxide layer and a mixture of silver and zinc on a portion of the sintered zinc oxide body where no copper oxide layer is formed, so as to form positive and negative electrodes; and heat-treating said positive and negative electrodes at a temperature of 550°–700° C. for 10 minutes to 1 hour.

* * * * *

UNITED STATES PATENT AND TRADEMARK OFFICE
CERTIFICATE OF CORRECTION

PATENT NO. : 5,576,067
DATED : November 19, 1996
INVENTOR(S) : Masaru Miyayama and Byoung C. Shin It is certified that error appears in the above-indentified patent and that said Letters Patent is hereby corrected as shown below:

Column 3 Line 15 "converted" should read --convert--.

Column 4 Line 40 "70° C." should read --700° C.--.

Column 4 Line 43 "were" should read --was--.

Signed and Sealed this

Sixth Day of May, 1997

*Attest:*

*Attesting Officer*

BRUCE LEHMAN

*Commissioner of Patents and Trademarks*